United States Patent [19]
Shields, Jr. et al.

[11] Patent Number: 6,080,403
[45] Date of Patent: Jun. 27, 2000

[54] PROTEASE CONTAINING HAIRBALL REMEDY AND USE THEREOF

[75] Inventors: Richard G. Shields, Jr.; Mark D. Newcomb, both of Newport, Ky.; Jeffrey P. Bennett, Corona, Calif.

[73] Assignee: Star-Kist Foods, Inc., Newport, Ky.

[21] Appl. No.: 09/240,865

[22] Filed: Feb. 1, 1999

Related U.S. Application Data

[60] Provisional application No. 60/089,758, Jun. 18, 1998.
[51] Int. Cl.$^7$ .................................................. A61K 38/46
[52] U.S. Cl. .................. 424/94.65; 424/94.1; 424/94.66
[58] Field of Search ............................... 424/94.1, 94.65, 424/94.66

[56] References Cited

PUBLICATIONS

Tiffer et al, Jama vol. 236 (14) p. 1578, Oct. 4, 1996.

*Primary Examiner*—Rebecca Cook
*Attorney, Agent, or Firm*—Burns, Doane, Swecker & Mathis, L.L.P.

[57] ABSTRACT

Animal food formulations, preferably dry cat foods and treats, or medicaments, e.g., tablets, gels or suppositories, that contain an amount of an enzyme (bromelain) effective to treat and/or prevent hairballs are provided. These formulations can be ingested chronically, i.e., daily, with no adverse effects.

17 Claims, No Drawings

PROTEASE CONTAINING HAIRBALL REMEDY AND USE THEREOF

This application claims priority under 35 U.S.C. §§119 (e) and or 365 to 60/089,758 filed in the United States on Jun. 18, 1998; the entire content of which is hereby incorporated by reference.

FIELD OF THE INVENTION

The subject invention pertains to animal food formulations and use thereof for alleviating hairballs in animals in need of such treatment, in particular cats, and most especially long-haired cats.

BACKGROUND OF THE INVENTION

Hairballs (trichobezoar) occur in many animals, including cattle, cats, rats, rabbits, primates, and humans. (Runnells et al, *Principles of Veterinary Pathology*, 7th Ed., The Iowa State University Press, Ames, Iowa, 1965; Anastasia et al, 1990; Newman et al, Gastric trichobezoars-sonographic and computed tomographic appearance. *Ped. Radiol.*, 20:526–527 1990.) Hairballs actually consist of a mixture of hair, mucous, food particles, and mineral salts. (Runnels et al, (Id.))

Hairballs result upon consumption of hair by an animal. This typically occurs as a result of dermatitis or the animal grooming itself or a companion animal. Because of the natural grooming behavior of some animals, such as rabbits and cats, hairballs are quite prevalent therein.

Not surprisingly, animals with lengthy coats are more predisposed to hairballs. However, hairballs can manifest themselves in animals having any length of hair.

Studies have shown that cats normally may spend as much as one-third of their waking hours cleaning and grooming themselves. Increased hair loss may occur as a result of disease (e.g., neuroses, excessive grooming, and dermatological related conditions) and because of normal seasonal fluctuations (molting) that may increase in the summer and decrease in the winter compared to spring or fall. (Hendricks, Protein metabolism in the adult domestic cat (Felis Catus), Ph.D. Thesis, Massey University, Palmerston North, New Zealand, 1996.) In cats, because of the structure of their tongue, a majority of this hair becomes consumed upon grooming. (Ducommun, The Cat's Body: The Versatile Tongue. *Cat Fancy*, pp 32–37, 1993). On average, studies have estimated that even domestic shorthaired cats lose an average of 28.1 g hair/kg body weight during the course of a year, two-thirds of which is consumed and expelled in the feces. This amount is obviously significantly greater in the long-haired cats.

Any ingested hair that is not digested or that does not otherwise pass down the digestive tract may accumulate in the stomach and form an overt hairball. The most common physiological consequences thereof are diarrhea and vomiting. (Lewis et al, Small Animal Clinical Nutrition U1, Mark Morris Associates, Topeka, Kans. 1987). However, in some instances, such as in rabbits, they may form an obstruction that can be life-threatening, absent surgical intervention.

Whether hairballs are a primary problem or a secondary manifestation of another underlying problem, such as gastric hypomobility, is a matter of debate. Conventional materials and methods for treating and preventing hairballs include the administration of lubricating agents which, in theory, should facilitate the trichobezoar in passing through the gastrointestinal tract. Also, another reported means of preventing and alleviating hairballs is the use of high fiber diets which ideally function to promote the motility of the digestive system and thereby expulsion of the hairball from the rectum. Related thereto, a product recently considered by several petfood manufacturers for preventing hairballs was reported, which is based on a combination of monounsaturated and polyunsaturated fatty acids, and for which preliminary data have suggested may reduce shedding.

Another nutritive product manufactured by Heinz, All Nature's Recipe® cat treats, contains canola oil and may provide a similar lubricant effect that promotes hairball expulsion. Additionally, All Nature's Recipe® pet foods products, including treats, are formulated to minimize adverse reactions to food (food allergies or intolerances) which may manifest themselves as dermatitis conditions. These include, by way of example, single meat protein sources in the products, natural preservative, and the absence of artificial colors, flavors and dairy products which may result in less hair loss attributable to self mutilation.

Still further, several treatments are available through various pet supply channels to prevent and/or treat hairballs. Many of these treatments are based on fiber supplementation which, as discussed above, increase the rate of passage through the intestinal tract. Hill's has endorsed this concept. (Lewis et al, (Id.)). The authors similarly report that other well known remedies for constipation may be beneficial, e.g., lubricants (mineral oil, petroleum jelly), and magnesium salts. (Lewis et al (Id.))

A problem associated with most conventional hairball treatment and prevention methods is that they tend to be anti-nutritional. They are anti-nutritional because they typically function to increase the passage of materials through the digestive tract thereby reducing nutrient digestion and absorption. Thus, better and more effective remedies for treating and preventing hairballs are needed.

Pineapple juice (Anauas comosus) has been anecdotally advocated for use in treating hairballs in rabbits. This juice is known to contain a variety of materials, including numerous proteinases. One of these proteinases is bromelain, a sulphydryl protease that can digest many proteins. However, pineapple juice contains at least four distinct cysteine proteinases, with the major stem one being stem bromelain, and the major fruit protease being fruit bromelain. Also, ananin and comasain are additional cysteine proteinases found in pineapple stem. (Rowan et al, *Biochem. J.*, The Cysteine Proteinases of the Pineapple Plant, 266(3): 869–875, 1990.)

Related thereto, some owners of cats and specially pets have reportedly used pineapple juice and also meat tenderizers, because of their wide availability allegedly to alleviate hairballs. Also, the *Merck Manual* recommends the use of 10 ml of fresh or frozen pineapple juice for treatment of rabbit hairballs for a three-day period. (Fraser, *Merck Veterinary Manual*, 7th Edition, Merck & Co., Rathway, N.J., 1991). Also, a regimen of hairball treatment involving pineapple juice administration in rabbits at a dosage of 5 ml for five days has been reported. (Harkness et al, *The Biology and Medicine of rabbits and Rodents*, 3rd Edition, Philadelphia, Pa., Lea and Febinger, pp 1–230 (1989). Still further, in a study involving a mature woman, a dosage of 900 ml/day reportedly reduced a bezoar to half its size in three weeks, and completely dissolved it in thirteen weeks. A dosage of 240 mg/day reportedly prevented reoccurrence. (Feffer et al, *JAMA*, 236:1578, (1976))

Still another reported regimen for treating hairballs involves the administration of psyllium seed (Petromalt).

Some persons have indicated that the active component contained therein is psyllium seed. However, earlier literature has suggested that diastase may instead be the active agent.

Probably the best prevention of hairballs, however, is daily brushing to remove loose hair, especially during late spring and early summer when shedding is prevalent.

Thus, based on the foregoing, various remedies have been reported for treatment and prevention of hairballs. Essentially, notwithstanding what has been reported, there still exists a need for improved treatments, i.e., which are pro-nutritional and which are convenient to the pet owner.

BRIEF DESCRIPTION OF THE INVENTION

Toward that end, the present inventors have elucidated that an enzyme that is found in some foods, including pineapple juice, i.e., bromelain, when added to pet foods, pet treats, and other materials for pet consumption, provides a highly effective pro-nutritional remedy of treating and prevent hairballs.

As discussed above, pineapple juice and other enzyme-containing materials have been anecdotally reported to have some benefits in the treatment and prevention of hairballs. However, to the best of the inventors' knowledge, there has been no reported usage of bromelain, a protease found in some foods, as a pro-nutritional, therapeutic additive to food formulations which are nutritionally suitable for consumption by pets, e.g., cats.

This constitutes a significant improvement to other conventional hairball treatments which typically adversely impact pet nutrition since they are designed to facilitate more rapid passage and expulsion of materials through the gastrointestinal system. In particular, the present invention provides animal food formulations adapted for consumption by animals prone to hairballs, preferably cats or rabbits, e.g., dry pet foods and pet treats, that contain an amount of a protease effective to prevent and/or treat hairballs when used appropriately, i.e., appropriate nutritive regimen.

More specifically, the present invention provides materials for consumption by animals prone to hairballs, preferably cats and rabbits, e.g., dry pet food materials, pet treats, that contain an amount of bromelain effective to prevent and/or treat hairballs when used appropriately.

Also, the present invention provides a regimen for preventing and alleviating hairballs in animals susceptible to hairball formation by feeding to such animals an effective amount of a protease, preferably bromelain, preferably contained in an animal food formulation, e.g., pet food or treat, or contained in the form of a pill that is effective to treat and/or prevent hairballs when administered at appropriate nutritive dosages.

More specifically, the present invention provides a regimen for treating animals that are susceptible to hairballs, e.g., cats and rabbits, comprising feeding to such animals a nutritional material, e.g., pet food or treat, or medicament, that contains an amount of bromelain that is effective to treat and/or prevent hairballs when administered appropriately.

DETAILED DESCRIPTION OF THE INVENTION

As discussed, the present invention generally relates to a pro-nutritional regimen for treating and/or preventing hairballs that involve feeding to animals susceptible to hairballs an animal food formulation that contains an amount of a protease, preferably bromelain, effective to treat and/or prevent hairballs when administered appropriately, i.e., when provided at amounts that provide for adequate nutrition.

A significant aspect of the invention is the fact that enzymes represent a pro-nutritional rather than anti-nutritional approach to hairball management. This is advantageous as it facilitates the administration thereof on a chronic basis, e.g., daily, without any adverse health effects. In fact, the daily administration of such enzymes in the form of pet foods or treats should facilitate digestion and thereby result in nutritional benefits.

In this regard, several enzymes have been previously evaluated for dietary supplementation in conjunction with poorly digested foodstuffs or with ingredients such as barley which increase viscosity of intestinal contents when fed to poultry. (Inborr, J. et al, Effect of enzyme treatment of piglet feeds on performance and post weaning diarrhoea, *Swedish J. Agr. Res.*, 18: 129–133, 1988; Classen et al, Enzyme use in poultry diets, *Proc. 25th Annual Nutr. Conf, For Feed Manufacturers*, Canadian Feed Industry Assn., pp 15–31, 1989; Inborr, Enzymes: Catalysts for pig performance, *Feed Management*, 41(2):22–30, 1990; Rotter, The future of crude enzyme supplements in pig nutrition, *Pig News and Information*, 11(1): 15–17, 1990; Classen, Growing interest in feed enzymes to lead to new products, *Feedstuffs*, 63(4): 22–25, 1991; Moodie, Boosting feed utilization: Choose your enzymes, *Feed Management*, 43(3):34–38, 1992; Han et al, Effect of enzyme supplementation on the utilization of high and low quality barley in pigs as measured by the mobile nylon bag technique, *J. Anim. Sci.*, 71(Suppl. 1):180, 1993; Vranjes et al, Influence of processing on dietary enzyme effect and nutrient value of diets for laying hens, *Can. J. Anim. Sci.*, 75:453:460, 1995; Ward, Enzyme use in viscous-inducing cereal diets examined, *Feedstuffs*, 67(49): 12–14, 1995; Ferket, Enzymes offer way to reduce waste, improve performance, *Feedstuffs*, 68(4):30–34, 1996; and Feord, Boosting digestibility: The use of enzymes in cereal-based dry dog foot, Petfood Industry, January/February Issue, 22–30, 1997.)

In selecting enzymes for oral administration to animals and humans, it is important that such enzyme exhibit stability and hydrolysis characteristics appropriate for the desired application. In the present context, the enzyme should exhibit appropriate shelf life stability and should maintain the desired proteolytic activity upon consumption by an animal prone to development of hairballs, such as cats, rabbits, and other animals having grooming habits that result in ingestion of appreciable amounts of hair. Many enzymes would be unsuitable for the present purposes as they are heat labile and/or labile under acid conditions. Also, the ingested enzyme desirably should contain an appropriate complex of enzymes which is customized for the particular diet. For example, it has been reported, with respect to phytase, an enzyme that reportedly improves plant phosphorus utilization, that the particular conditions affect is relative effectiveness.

Based on the results disclosed infra, bromelain is well suited for the intended application, i.e., a pro-nutritional remedy for alleviating and preventing hairballs in susceptible animals. Bromelain is actually a complex of different compounds which has been previously evaluated for other therapeutic usage, in particular as an anti-inflammatory (similar to aspirin and omega-3 fatty acids), immune enhancement, burn recovery, cardiovascular health, cancer, roundworm therapy, arthritis, and pancreatic insufficiency. It is also used to produce "chill proof" beer because of its role in hydrolyzing protechtennin complexes (Heinicke et al, Stem bromelain-A new protease preparation from pineapple plants, *Economic Botany*, 11:225–234, 1957). Both bromelain and papain have been used commercially for their protein hydrolysis function. However, bromelain is superior thereto with respect to color, odor and availability. (Hunter et al, *Amer. J. Obstetrics and Gynecol.*, 73:867–874, 1957).

While its complex composition has not been fully elucidated, bromelain is considered to be a thiol-group protease. The activity of this enzyme is standardized based on its casein digesting ability (casein-digesting units). Bromelain has an approximate molecular weight of 22,500 (Wharton, The structure and mechanism of stem bromelain: Evaluation of the homogeneity of purified stem bromelain, determination of molecular weight and kinetic analysis of the bromelain-catalyzed hydrolysis of n-benzyloxycarbonyl-L-phenylalanyl-L-serine methyl ester, *Biochem. J.*, 143:575–586 1974; Arroyo-Reyna et al, Circular dichroism of stem bromelain: A third spectral class within the family of cysteine proteinases, *Biochem. J.*, 300(Pt-1):107–110, 1994).

Bromelain is effective for dissolving hairballs based on its hydrolytic activity. Specifically, in addition to its ability to digest keratin proteins such as hair, it also apparently facilitates mucous digestion. (Previously, it has been used in which to digest mucous in the uterus to improve radiographs (Hunter et al (Id.)). This also should be beneficial in the present context because, as noted previously, hairballs consist of a mixture of hair, mucous, food particles and mineral salts.

Bromelain, in order to be effective for the intended application, should also resist denaturation in the stomach. In previous studies, bromelain has been observed to be effectively absorbed and to circulate to a target organ, with the absorption of the protease complex being estimated to be about 40% (Lotz-Winter, On the pharmacology of bromelain: An update with special regard to animal studies on dose-dependent effects, *Plant Med.*, 56:249–253, 1990).

Crude bromelain extracts contain at least eight different proteolytically active compounds, which possess different optimal pH's ranging from acidic to basic, and also exhibiting different protein specificity. (Taussig et al, Bromelain: A proteolytic enzyme and its clinical application. A review., *Hiroshima J Med. Sci.*, 24:185–193, 1975; Barbarino et al, The influence of bromelain on digestion and absorption in control animals and in methotrexate-induced "cytostatic" enteropathy, *J. Nuclear Med. and Allied Sci.*, 26:97–103, 1982; Harrach et al, Isolation and partial characterization of basic proteinases from stem bromelain, *J. Protein Chem.*, 14:41–52, 1995; Heinicke et al, Stem bromelain-A new protease preparation from pineapple plants, *Economic Botany*, 11:225–234, 1957.)

Based on the wide pH activity range of bromelain, this enzyme should facilitate digestion of proteins during their entire passage through the esophagus, stomach, and intestinal tract. As noted, this is advantageous in the present context since hairballs not only contain hair, but also undigested food particles. Bromelain is also advantageous in the present context because it is approved for use in animal feeds including pet foods (AAFCO, 1997), and because it is relatively non-toxic. In fact, bromelain has no established LD50 dosage. At levels up to 10 g/kg b.w./day the enzyme does not elicit any undesirable side effects and is non-carcinogenic or teratogenic.

Thus, based on the foregoing, bromelain has numerous beneficial characteristics that facilitate its usage as a pro-nutritional remedy for preventing and/or treating hairballs in animals in need of such treatment.

In general, bromelain will be added to animal food formulations or to medicaments that are suitable for ingestion by animals susceptible to hairballs, including by way of example cats, rabbits, primates and other zoo animals and pets, in an amount effective to prevent and/or treat hairballs when the food formulation or medicament is administered under appropriate guidelines, e.g., daily consumption amounts that provide for appropriate nutrition.

Bromelain can be added to any food formulation adapted for animal consumption. However, it is preferable that it not be added in canned formulations.

This is because bromelain is thought to be stable to the heat associated with pelleting (used to make dry feed) but not at temperatures generally associated with extrusion which may exceed 170° C. Based on this fact, bromelain will preferably be added post-extrusion in dry-extruded pet food applications. Also, bromelain can be provided in the form of a medicament, e.g., a tablet, a gel, or a suppository by the use of conventional excipients and carriers.

While bromelain has no reported undesirable side effects, because it is a protein appropriate care should be taken to prevent plant workers who handle the raw powder from potentially developing allergic reactions. This can be effected, e.g., by use of masks to prevent breathing in of raw powder, gloves, and other known methods for preventing contact with the enzyme powder. The design of appropriate operating conditions is well within the level of ordinary skill in the art as such conditions are conventionally used in the handling of enzyme powders.

As noted, bromelain will be provided in the form of a medicament, e.g., a tablet, or will be added to an animal food formulation, preferably a dry food material post-extrusion, that is nutritionally suitable for administration to an animal prone to hairballs, e.g., cats, rabbits, primates, and other zoo animals and specialty pets to produce an animal food formulation that contains an effective amount of the enzyme to prevent and/or treat hairballs when ingested at appropriate daily dosages, i.e., dosages that provide for appropriate nutrition when used as a primary or supplementary nutrient sources.

The selection of an appropriate enzyme dosage will depend on factors including the size of the animal, the type of animal, its relative susceptibility to hairballs, and whether this food is a primary food source or a supplementary food source (e.g., a pet food treat).

In the case of cats, the bromelain material will be added in a concentration to provide an average daily dosage ranging from about 0.2 to 2,200 cdu/day (cdu=casein digesting units), more preferably about 0.5 to 220 cdu/day, and most preferably about 1 to 100 cdu/day. For example, the recommended daily dosage for an eight pound cat is approximately 2 cdu of bromelain per day.

Bromelain can also be added to pet foods and treats for other animals prone to hairballs, e.g., rabbits, guinea pigs, hamsters, gerbils, primates and other zoo animals. The bromelain dosage will again be selected to produce a daily dosage optimal for the particular animal. For instance, in the case of a rabbit, this daily dosage will range from about 25 to 50,000 cdu/day, more preferably about 75 to 5000 cdu/day and most preferably about 125 to about 1000 cdu/day. More specifically, a suitable dosage for a dry rabbit food formulation will give an average daily bromelain dosage of about 250 cdu/day.

Based on the pro-nutritional characteristics of bromelain and absence of adverse side effects, the subject bromelain-containing pet foods and treats can be used repeatedly, i.e., daily.

The animal food formulations according to the invention, e.g., dry food pellets and treats will be designed such that they contain appropriate nutrition levels for the particular animal, e.g., a cat or rabbit. In this regard, the design of animal food formulations for particular animals, e.g., cats, rabbits, etc., is well known and established. There exist accepted nutritional guidelines for optimal amounts of proteins, fats, vitamins, minerals, fibers, that vary dependent upon the particular animal and its age and health. It is anticipated that bromelain can be added to any animal food formulation adapted for administration to an animal prone to hairballs.

As noted, a preferred example thereof is cat food formulations. Such pet foods and treats will comprise ingredients, typically used therein, e.g., grain materials, such as soy, rice, wheat, barley, corn, sorghum, oats, and triticate, meat and other animal by-products of poultry, beef, pork, dairy venison, rabbit, lamb, duck origin, vitamins (such as vitamin A, vitamin E, choline chloride, niacin, ascorbic acid, thiamine, biotin, vitamin B12, vitamin D3, d-calcium pantothenate riboflavin, inositol, pyridoxine hydrochloride, folic acid, menadion sodium bisulfate complex, minerals (such as zinc, phosphorous, iron, copper, manganese, calcium, and selenium-containing materials; salts, such as calcium carbonate, dicalcium phosphate, calcium sulfate, potassium citrate, monocalcium phosphate, sodium chloride, microbial extracts such as Lactobillus acidophilous, Streptococcus faecium, Bacillus subtilis, Aspergillus oryzae, Aspergillus niger, other plant extracts such as Yucca, oils, stabilizers such as BHA, BHT, tocopherols, citric acid, and flavoring agents such as herbs. Preferred materials also used in cat food formulations include, by way of example, corn gluten meal, lard, tallow, poultry fat, canola oil, fish oil, corn oil, soybean oil, brewers yeast, fish meal, and amino acids.

Preferred materials used in gerbit/hamster/rabbit foods include, by way of example, alfalfa, dehydrated alfalfa meal, alfalfa hay, molasses, clover, and clover hay. This list is meant to be exemplary and not exhaustive.

Also, in the case of rabbits, the food formulation should provide the following preferred protein, fiber, fat and carbohydrate ranges:

|  | Ranges, % |
| --- | --- |
| Protein | 10–20 |
| Fiber | 10–25 |
| Fat | 1–8 |
| Carbohydrate | 30–60 |

Accordingly, in the present invention, the particular food will, of course, be designed to provide suitable protein, fat, and fiber percentages which will vary dependent upon the age and health of the animal, and the type of animal.

A particularly preferred cat food composition according to the invention comprises the Nature's Recipe® material which is a high fat, nutritionally balanced cat treat containing formulation. This formulation is designed to reduce adverse food reactions. Therefore, this food should also further reduce shedding and dermatitis, thereby reducing grooming and further aiding the prevention of hairball formation.

As noted, the subject bromelain-containing food compositions will preferably be administered chronically, i.e., daily, in order to prevent and/or treat hairballs. This should prevent or alleviate the adverse side effects associated therewith which include diarrhea and vomiting, and poor digestion. This should enhance the overall health of the animal as well as affording aesthetic benefits, i.e., reduced staining of carpets, furniture, and other household items which may result as a consequence of such activities.

The invention will now be described in more detail in the following Examples.

EXAMPLE 1

Materials and Methods

A letter was sent to area animal hospitals near the study center requesting referral of feline patients with known histories of hairball problems, as determined by the animal's owner, for inclusion in the study.

Sixteen cats were referred ranging in age from 1.5 to 13 years. There were 5 spayed females, & 7 neutered males and 4 intact females. Seven of the cats were long-haired, 7 were medium-haired and 2 were short-haired. These animals were on the study for 25–72 days.

Physical examinations, complete blood cell counts, electrolyte panels and several feline hormonal and viral screens were performed on each cat at the beginning and the end of the survey period. Thoracic and abdominal radiographs were taken on each cat at the beginning of the research period.

Participants were fed four treats SID, with each treat containing 0.22 cdu of bromelain. Owners of the cats were surveyed at one and two month intervals requesting information regarding the following: attitude, appetite, change in frequency of hairball vomition, previous hairball remedies utilized and their efficacy.

Results

Physical examination data was unremarkable for most cats, although two animals did have evidence of advanced dental tartar and one of these same animals was also missing multiple teeth.

Radiographic evaluation was made of the thoracic and abdominal cavities of each study participant. While the vast majority of abdominal and thoracic radiographs were normal, two cats did have urinary cystic calculi. Radiographs of two other cats revealed "probable" gastric hairballs, and one of these same two animals also had evidence of feline asthma.

The effects of bromelain on vomiting frequency in cats with a history of problems with hairballs are shown in Table 1. Owners reported a marked decrease in the frequency of vomition in cats receiving the bromelain treats at the end of both the first survey period 64% and the second survey period 84%.

A summary of the hematological tests performed at the initiation and end of the study is shown in Table 2. A decrease in WBC count was noted in 4 cats at the initiation of the study and in 5 cats at the end of the study. This measurement is consistent with a stress leukograin. The incidence of low (L), normal (N) and high (H) values of the other hematological parameters are shown. There is no general pattern of abnormality suggesting an increase in specific disease syndromes in this population of cats. Similarly, comparison of pre- and post-study bloodwork also shows no major trends or consistent abnormalities, which might be specifically attributable to the bromelain administration.

The present study suggests that feeding bromelain treats markedly reduces the frequency of vomiting in cats having a preexisting problem with hairballs.

Conclusions

Bromelain containing treats fed on a daily basis to cats with a history of vomiting hairballs reduced the frequency of vomiting by 62.5% at one-month and 81.3% at two months. The treats were well tolerated in most cats. However, other flavors might improve their acceptance in a small number of cats that lost interest in the treats. No deleterious side effects attributable to the bromelain treats were noted. Moreover, compared to some other commercially available hairball remedies, the bromelain was easier for owners to administer which itself might promote a more consistent consumption and efficacy.

TABLE 1*

| Vomiting | Initial Survey | | Second Survey | |
|---|---|---|---|---|
| Frequency | No. | % | No. | % |
| Less | 10 | 62.5 | 13 | 81.3 |
| Same | 6 | 37.5 | 3 | 18.7 |
| More | 0 | 0 | 0 | 0 |
| TOTAL | 16 | 100 | 18 | 100 |

*Effect of Bromelain on Vomiting Frequency in Cats With A History of Hairball Problems.

TABLE 2

Summary of Hematological Findings in Cats with Historical Problems with Hairballs

| | | # Of Cats And Values - Start of Study | | | # of Cats And Values End of Study | | |
|---|---|---|---|---|---|---|---|
| Test | Adult Feline Normals | L | N | H | L | N | H |
| WBC | 5.5–19.5 × 1000/UL | 4 | 12 | 0 | 5 | 0 | 1 |
| RBC | 6.5–10.5 × 1000/UL | 0 | 16 | 0 | 0 | 15 | 1 |
| HGB | 9.0–15.0 × 1000/UL | 0 | 15 | 1 | 0 | 16 | 0 |
| PCV | 37–45% | 0 | 15 | 1 | 0 | 15 | 1 |
| MCV | 39–55 FL | 0 | 16 | 0 | 0 | 15 | 1 |
| MCH | 12.5–17.SPG | 0 | 16 | 0 | 0 | 16 | 0 |
| MCHC | 32–36% | 1 | 15 | 0 | 0 | 16 | 0 |
| NEUTROPHELS | 2.5–12.5 × 1000/UL | 1 | 15 | 0 | 1 | 15 | 0 |
| LYMPHOCYTES | 1.5–7.0 × 1000/UL | 3 | 13 | 0 | 5 | 10 | 1 |
| MONOCYTES | 0–850/UL | 0 | 16 | 0 | 0 | 16 | 0 |
| EOSINOPHIILS | 0–800/UL | 0 | 15 | 1 | 0 | 14 | 2 |
| PLATELET EST. | Adequate | 0 | 16 | 0 | 0 | 16 | 0 |
| SGOT | 10–100 U/L | 0 | 16 | 0 | 0 | 15 | 1 |
| ALT | 10–100 U/L | 0 | 15 | 1 | 0 | 16 | 0 |
| TOTAL BILIRUBIN | .1–6 mg/dL | 1 | 15 | 0 | 5 | 11 | 0 |
| SAP | 20–100 U/L | 2 | 13 | 0 | 0 | 16 | 0 |
| GGT | 1–10 IU/L | 0 | 16 | 0 | 0 | 16 | 0 |
| TPP | 5.3–7.9 g/dL | 0 | 16 | 0 | 0 | 16 | 0 |
| ALBUMIN | 2.6–5.6 g/dL | 0 | 14 | 2 | 0 | 13 | 3 |
| GLOBULIN | 2.6–5.6 g/dL | 0 | 16 | 0 | 0 | 14 | 2 |
| A/G RATIO | 0.5–1.2 | 0 | 15 | 1 | 1 | 15 | 0 |
| CHOLESTEROL | 90–150 mg/dL | 2 | 9 | 5 | 0 | 11 | 5 |
| BUN | 10–30 mg/dL | 0 | 15 | 1 | 0 | 16 | 0 |
| CREATININE | 0.8–2.0 mg/dL | 0 | 16 | 0 | 0 | 14 | 2 |
| BUN/ CREATININE | 5–38 | 0 | 16 | 0 | 0 | 16 | 0 |
| PHOSPHORUS | 2–6.5 mg/dL | 0 | 16 | 0 | 0 | 16 | 0 |
| CALCIUM | 8.2–11 mg/dL | 0 | 13 | 1 | 0 | 13 | 3 |
| CALCIUM/P0$_4$ | 1.3–5.7 | 0 | 16 | 0 | 0 | 16 | 0 |
| GLUCOSE | 75–160 mg/dL | 0 | 15 | 1 | 0 | 16 | 0 |
| AMYLASE | 20–200 IU/L | 0 | 14 | 2 | 0 | 15 | 1 |
| LIPASE | 25–450 IU/L | 0 | 14 | 2 | 0 | 13 | 3 |
| SODIUM | 146–155 mEq/L | 1 | 15 | 0 | 0 | 16 | 0 |
| POTASSIUM | 3.7–5.2 mEq/L | 0 | 13 | 3 | 0 | 16 | 0 |
| NA/K RATIO | 32–41 | 0 | 16 | 0 | 0 | 16 | 0 |
| CHLORIDE | 115–125 mEq/L | 3 | 12 | 1 | 2 | 14 | 0 |
| CPK | 20–400 IU/L | 0 | 12 | 4 | 0 | 9 | 7 |
| OSMOLALITY | 285–320 MosM/kg | 0 | 14 | 2 | 0 | 16 | 0 |
| T4 (RIA) | .8–4.0 Ug/dL | 1 | 15 | 0 | 0 | 16 | 0 |
| HEMOBART. | Negative | 0 (+), 16 (−) | | | 0 (+), 16 (−) | | |

TABLE 2-continued

Summary of Hematological Findings in Cats with Historical Problems with Hairballs

| | | # Of Cats And Values - Start of Study | # of Cats And Values End of Study |
|---|---|---|---|
| Test | Adult Feline Normals | L N H | L N H |
| FELV | Negative | 0 (+), 16 (−) | 0 (+), 16 (−) |
| FIV | Negative | 1 (+), 15 (−) | 0 (+), 15 (−), 1 N/A |
| FIP | Negative | 1 (+), 15 (−) | 2 (+), 14 (−) |

NOTE: cats #1, 20 and 24 do not have bloods yet.

EXAMPLE 2

This Example provides the details of a preferred bromelain-containing cat food formulation according to the invention, i.e., Nature's Recipe®.

NATURE'S RECIPE
IVD VETERINARY FORMULA FELINE TREAT FORMULA:

| Ingredient | Spec | % |
|---|---|---|
| Chicken Meal | 50774 | 24.1600 |
| Long Grain Rice | 50776 | 21.5200 |
| Crk Prealed barley | 50773 | 21.5200 |
| Soybean Meal | 50401 | 10.0000 |
| Poultry Fat | 50895 | 8.8771 |
| Dried Whole Egg | 50518 | 4.0000 |
| Digest Poultry | 51054 | 4.0000 |
| Calcium Carbonate | 50244 | 1.2800 |
| Canola Oil | 50220 | 1.0000 |
| Tomato pomace | 50775 | 1.0000 |
| Brewers Yeast | 50108 | 0.9000 |
| Salt-Food grade | 50007 | 0.5000 |
| Choline Chloride, 60% | 50469 | 0.4000 |
| Potassium Chloride | 50243 | 0.2000 |
| Bromelain | 51065 | 0.2000 |
| Taurine | 50150 | 0.0929 |
| Lacto Sacc | 50771 | 0.1000 |
| NR/IVD-Vit-DCF-S | 50848 | 0 1000 |
| NR/IVD-Min-Mix-DCF | 50851 | 0.1000 |
| Naturox, dry | 50326 | 0.0400 |
| Yucca Schidigera | 50772 | 0.0100 |
| Total | | 100.0000 |

More specifically, the Nature's Recipe® cat food formulation contains the following ingredients: Chicken Meal, Ground Rice, Cracked Pearled Barley, Soybean Meal, Chicken Fat (Preserved with mixed tocopherols, Rosemary Extract and Citric Acid), Dried Egg Product, Natural Flavor, Calcium Carbonate, Canola Oil, Tomato Pomace, Brewers dried Yeast, sodium chloride, Potassium chloride, Bromelain. Taurine, *Lactobacillus acidophilus*, Entrococcus Faecium, *Bacillus subtilis* fermentation extract, *Aspergillus oryzae* fermentation extract, *Aspergillus niger* fermentation extract, *Yucca schidigera* extract, vitamins (choline chloride, vitamin E supplement, niacin supplement, ascorbic acid, d-calcium pantothenate, thiamine mononitrate, riboflavin supplement, vitamin A supplement, inositol, pyridoxine hydrochloride, folic acid, menadione sodium bisulfite complex (source of vitamin K activity), biotin, vitamin B12 supplement, vitamin D3 supplement), minerals (zinc proteinate, ferrous sulfate, iron proteinate, zinc oxide, copper proteinate, copper sulfate, manganous oxide, calcium iodate, sodium selenite). These materials are formulated to produce a feed having the following minimum and maximum protein, fat, fiber and moisture percentages. This feed is suitable for daily consumption, and provides a complete and balanced nutritional material.

| | | |
|---|---|---|
| Crude Protein | Min. | 28.0% |
| Crude Fat | Min. | 15.0% |
| Crude Fiber | Max. | 4.0% |
| Moisture | Max | 10.0% |

Upon production, each treat will weight about 0.485 grams. On average, about 12 treats provides about 10% of daily calorie needs for an average weight (8 lb) cat. This material contains about 0.2% of bromelain, having an activity of about 240 MDU (casein-digesting units).

While the invention has been described with respect to certain specific embodiments, it will be appreciated that many modifications and changes thereof may be made by those skilled in the art without departing from the spirit of the invention. It is intended, therefore, by the appended claims to cover all modifications and changes that fall within the true spirit and scope of the invention.

What is claimed is:

1. An animal food formulation with appropriate nutritional values for an animal prone to hairball formulation when used as a primary or supplementary nutrient source which comprises an amount of bromelain effective to prevent or treat hairballs when administered at appropriate daily dosage.

2. The animal food formulation of claim 1, which comprises an average protein composition ranging from 5 to 45%; an average fat composition ranging from 2 to 25%, and an average fiber composition ranging from 1 to 25%.

3. The animal food formulation of claim 1, which provides for an average daily dosage of bromelain ranging from 0.5 to 220 cdu/day, when ingested at appropriate daily dosages.

4. The animal food formulation of claim 1, which is a dry food formulation suitable for usage as a primary nutrient material in an animal selected from the group consisting of cats, rabbits, guinea pigs, hamsters, gerbils.

5. The animal food formulation of claim 4, which is a dry cat food.

6. The animal food formulation of claim 4, which is a dry rabbit food formulation.

7. The animal formulation of claim 1, which is adopted for usage as a supplementary nutrient material.

8. The animal food formulation of claim 7, which is a cat treat composition.

9. The animal food formulation of claim 1, which is in the form of pellets.

10. The animal food formulation of claim 9, wherein the bromelain is added to said pellets post-extrusion.

11. A method of treating or preventing hairballs in an animal susceptible thereto comprising feeding to such animal an effective amount of an animal food formulation according to claim 1.

12. The method of claim 11, wherein the animal is selected from the group consisting of cats, rabbits, guinea pigs, hamsters and gerbils.

13. The method of claim 12, wherein the animal is a cat.

14. The method of claim 11, wherein said animal food formulation is a dry cat food or cat treat.

15. The method of claim 11, wherein the food formulation is designed to provide for an average bromelain daily dosage ranging from 0.5 to 220 cdu/kg daily, when ingested at appropriate daily dosages.

16. A method of treating or preventing hairballs in an animal in need of said treatment comprising administering to said animal bromelain in tablet form for a time effective to prevent or treat hairballs.

17. The method of claim 16, wherein the animal is a cat.

* * * * *